(12) United States Patent
Gilboa

(10) Patent No.: US 6,887,236 B2
(45) Date of Patent: May 3, 2005

(54) MULTIPLE-ELECTRODE CATHETER ASSEMBLY AND METHOD OF OPERATING SUCH A CATHETER ASSEMBLY

(76) Inventor: Pinhas Gilboa, 8 Tzidkiyahu St., Haifa 34409 (IL)

( * ) Notice: Subject to any disclaimer, the term of this patent is extended or adjusted under 35 U.S.C. 154(b) by 245 days.

(21) Appl. No.: 10/137,415

(22) Filed: May 3, 2002

(65) Prior Publication Data

US 2003/0208102 A1 Nov. 6, 2003

(51) Int. Cl.⁷ .............................................. A61B 18/18
(52) U.S. Cl. ........................................ 606/41; 128/898
(58) Field of Search ...................... 606/27–52

(56) References Cited

U.S. PATENT DOCUMENTS

| | | | |
|---|---|---|---|
| 5,341,807 A | | 8/1994 | Nardella |
| 5,433,198 A | | 7/1995 | Desai |
| 5,555,883 A | | 9/1996 | Avitall |
| 5,842,984 A | | 12/1998 | Avitall |
| 5,893,885 A | * | 4/1999 | Webster, Jr. ............... 607/122 |
| 6,319,250 B1 | * | 11/2001 | Falwell et al. ................ 606/41 |
| 6,666,864 B2 | * | 12/2003 | Bencini et al. ............... 606/41 |
| 6,751,492 B2 | * | 6/2004 | Ben-Haim ................... 600/374 |

FOREIGN PATENT DOCUMENTS

| | | |
|---|---|---|
| WO | WO00/10456 | 3/2000 |
| WO | WO00/16684 | 3/2000 |

* cited by examiner

*Primary Examiner*—Michael Peffley
*Assistant Examiner*—Pete Vrettakos
(74) *Attorney, Agent, or Firm*—Mark M. Friedman

(57) ABSTRACT

A multiple-electrode catheter assembly includes a hollow catheter having an internal elongated channel and a flexible distal portion. A number of electrodes are spaced along the flexible distal portion. An inner element, slidingly engaged within the elongated channel, has a steering mechanism configured for selectively deflecting a steerable distal portion of the inner element. According to additional, or alternative, features, the inner element includes sliding contacts for forming electrical connections with the electrodes, and displaceable locating elements for determining the position of an electrode during operation. Also provided is a method for operating such a catheter.

31 Claims, 10 Drawing Sheets

MULTIPLE-ELECTRODE CATHETER ASSEMBLY AND METHOD OF OPERATING SUCH A CATHETER ASSEMBLY

FIELD AND BACKGROUND OF THE INVENTION

The present invention relates to catheters for performing tissue ablation and, in particular, it concerns a multiple-electrode catheter assembly and a method of using a multiple-electrode catheter assembly.

Atrial fibrillation is, in many cases, treated by ablating atrial tissue at a plurality of locations along a line so as to form a closed loop of ablation across the atrium. In other cases, it is treated by ablating the pulmonary vein tissue at a plurality of locations along a line, so as to form a closed loop of ablation across the vein.

PCT Publication No. WO00/16684, which is incorporated by reference as if fully set forth herein, teaches how to mark and ablate a series of points of ablation in order to create a continues line of ablation. According to WO00/16684 this is effected by a steerable catheter having a tip adapted to ablate a single point. It is very difficult, however, to achieve sufficient precision to ensure ablation of a contiguous line of tissue using a single electrode catheter. Furthermore, the repeated repositioning of the catheter between successive ablation steps is very time consuming.

In an alternative approach to ablation of a line of tissue, a number of multiple-electrode catheters have been proposed to allow successive ablation of multiple sites while the catheter is in a single position. Examples of such devices may be found in U.S. Pat. Nos. 5,842,984; 5,555,883; 5,893,885; 5,433,198 and 5,341,807, which are incorporated by reference as if fully set forth herein. Each of these teaches a multiple-electrode catheter designed to ablate a tissue at a plurality of locations along a line of predetermined configuration. In some cases, this configuration is monitored by sensors adapted for determining the shape or curvature of the portion of the catheter carrying the multiple electrodes. These multiple-electrode catheters are positioned in contact with the endocardium tissue where ablation is performed in a controlled manner, typically one electrode at a time. Typically, the parameters of the process, such as current, voltage, and temperature are monitored at each individual point of ablation, thereby giving an indication of the quality of ablation at each point.

Although the use of a multiple-electrode catheter provides a partial solution to the difficulty in forming a contiguous line of ablation, significant problems are still encountered. Most significantly, it often occurs that one or more of the electrodes is not properly in contact with the endocardium when actuated and, as a result, insufficient ablation occurs. This results in a break in the line of ablation which may cause the entire procedure to fail. In order to facilitate re-treatment of a site not properly treated by the device, it is possible to include multiple location sensing elements adjacent to the electrodes to record the position of each point treated. This however, would add very greatly to the cost of the device. Finally, even without multiple location sensing elements, the structure of a multiple-electrode catheter is complicated by the need for multiple electrical wires along the entire length of the catheter and corresponding multiple electrical connections. Each electrode requires its own electrical connection. Furthermore, if a thermistor is to be provided for each electrode, a further two wires are required. As a result, a ten electrode catheter typically requires 30 wires passing along its length. This presents a considerable design problem for a catheter of a few millimeters diameter, and results in high production costs. Since such catheters are typically disposable items intended for a single use, the use of such catheters adds significantly to the cost of the procedure.

There is therefore a need for a multiple-electrode catheter assembly and method of operating such a catheter assembly which would ensure reliable contact between each electrode and the corresponding region of tissue during actuation of the electrode.

SUMMARY OF THE INVENTION

The present invention is a multiple-electrode catheter assembly and a method for performing a procedure using such a catheter assembly.

According to the teachings of the present invention there is provided, a multiple-electrode catheter assembly comprising: (a) a hollow catheter having an internal elongated channel and a flexible distal portion, a plurality of electrodes being spaced along the flexible distal portion; and (b) an inner element slidingly engaged within the elongated channel, the inner element having a steering mechanism configured for selectively deflecting a steerable distal portion of the inner element.

According to a further feature of the present invention, the steering mechanism is configured to be selectively operable from an initial curved form so as to tend to straighten the steerable distal portion.

According to a further feature of the present invention, the plurality of electrodes is implemented as n electrodes spaced evenly at an interval d along the flexible distal portion, n being at least 3, and wherein a distal end and a proximal end of the steerable distal portion are separated by a length L along the inner element, L being approximately equal to m×d where m is a positive integer less than n, such that the distal end and the proximal end of the steerable distal portion come into simultaneous functional alignment with pairs of the electrodes.

According to a further feature of the present invention, m is no more that half of n such that each one of the electrodes is spaced by L from at least one other of the electrodes.

According to a further feature of the present invention, the inner element further includes a distal electrical contact located at the distal end of the distal steerable portion and a proximal electrical contact located at the proximal end of the distal steerable portion, the distal and the proximal electrical contacts being configured such that, by moving the inner element along the internal elongated channel, the distal and proximal electrical contacts are selectively brought into alignment for forming an electrical connection with the pairs of the plurality of electrodes.

According to a further feature of the present invention, the inner element further includes a distal locating element located at the distal end of the distal steerable portion and a proximal locating element located at the proximal end of the distal steerable portion, the distal and the proximal locating elements forming parts of a location sensing system for determining positions of the distal end and the proximal end, respectively, of the steerable distal portion.

There is also provided according to the teachings of the present invention, a multiple-electrode catheter assembly comprising: (a) a hollow catheter having an internal elongated channel and a hollow distal portion, a plurality of electrodes being spaced along the hollow distal portion; and (b) an inner element slidingly engaged within the elongated channel, the inner element having an actuating distal portion including at least one outwardly facing electrical contact, the electrical contact being configured such that, by moving the inner element along the internal elongated channel, the electrical contact is selectively brought into alignment for forming an electrical connection with each of at least two of the plurality of electrodes.

According to a further feature of the present invention, the plurality of electrodes is implemented as n electrodes spaced evenly at an interval d along the flexible distal portion, n being at least 3, and wherein the at least one electrical contact includes a distal electrical contact and a proximal electrical contact separated by a length L along the inner element, L being equal to m×d where m is a positive integer less than n, such that the distal electrical contact and the proximal electrical contact of the actuating distal portion come into simultaneous alignment with pairs of the electrodes.

There is also provided according to the teachings of the present invention, a multiple-electrode catheter assembly comprising: (a) a hollow catheter having an internal elongated channel and a hollow distal portion, a plurality of electrodes being spaced along the hollow distal portion; and (b) an inner element slidingly engaged within the elongated channel, the inner element having a sensing distal portion including at least one locating element, the locating element forming part of a location sensing system for determining a position of at least one point within the inner element, such that, by moving the inner element along the internal elongated channel, the locating element is selectively brought into alignment for determining the position of each of at least two of the plurality of electrodes.

According to a further feature of the present invention, the plurality of electrodes is implemented as n electrodes spaced evenly at an interval d along the flexible distal portion, n being at least 3, and wherein the at least one locating element includes a distal locating element and a proximal locating element separated by a length L along the inner element, L being equal to m×d where m is a positive integer less than n, such that the distal locating element and the proximal locating element of the sensing distal portion come into simultaneous alignment with pairs of the electrodes.

According to a further feature of the present invention, the at least one locating element forms part of a locating system which determines the position of at least one point in the inner element in three dimensions.

According to a further feature of the present invention, the at least one locating element forms part of a locating system which is a non-imaging locating system.

According to a further feature of the present invention, the at least one locating element forms part of a locating system which generates coordinates of the position of at least one point relative to a given frame of reference.

There is also provided according to the teachings of the present invention, a method for performing a procedure using a multiple-electrode assembly, the method comprising: (a) providing a hollow catheter having a distal portion with a plurality of independently operable electrodes; (b) deploying a steering mechanism within the hollow catheter so as to be slidable along a length of the distal portion; (c) guiding the catheter to a position in which each of the electrodes lies adjacent to a corresponding region of tissue; (d) sliding the steering mechanism along the distal portion to a first position and actuating the steering mechanism so as to ensure effective contact of at least a first of the electrodes with the corresponding region of tissue during operation of the first electrode; and (e) sliding the steering mechanism along the distal portion to a second position and actuating the steering mechanism so as to ensure effective contact of at least a second of the electrodes with the corresponding region of tissue during operation of the second electrode.

According to a further feature of the present invention, the catheter assumes a curved configuration when in the position in which each of the electrodes lies adjacent to a corresponding region of tissue, and wherein the steering mechanism is actuated so as to tend to straighten a selected part of the distal portion.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is a multiple-electrode catheter assembly and a method for performing a procedure using such a catheter assembly.

The principles and operation of catheter assemblies according to the present invention may be better understood with reference to the drawings and the accompanying description.

Figure 1A:
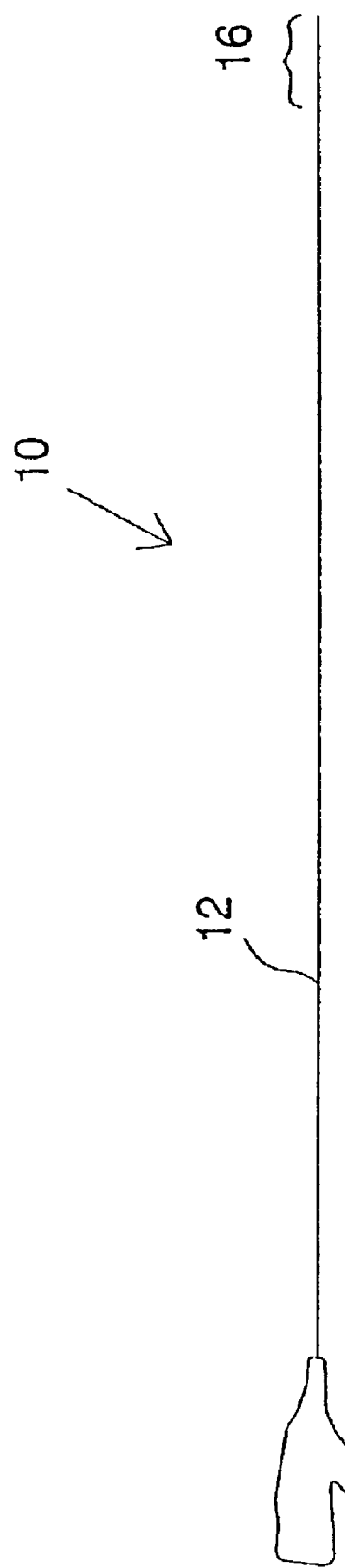
FIG. 1A is a schematic side view of a preferred implementation of a multiple-electrode catheter assembly, constructed and operative according to the teachings of the present invention.
Figure 1B:
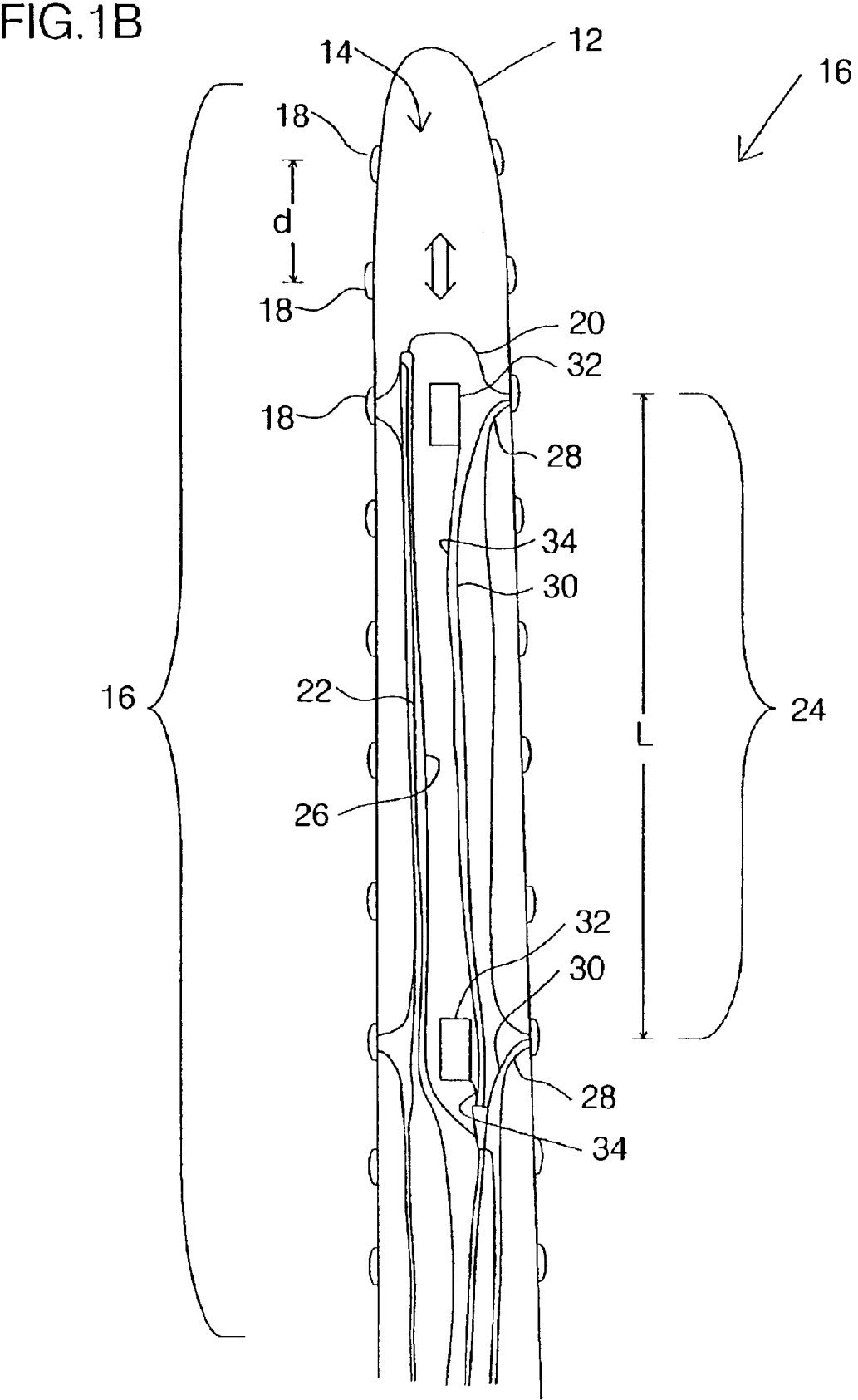
FIG. 1B is an enlarged cross-sectional view taken through a distal portion of the catheter assembly of FIG. 1A.

Referring now to the drawings, FIGS. 1A and 1B show a multiple-electrode catheter assembly, generally designated 10, constructed and operative according to the teachings of the present invention. Generally speaking, catheter assembly 10 includes a hollow catheter 12 with a flexible distal portion 16. The portion of catheter 12 proximal to distal portion 16 is generally standard and is shown here only schematically. Catheter 12 has an internal elongated channel 14 extending along substantially its entire length, best seen in FIG. 1B. A plurality of electrodes 18 are spaced along distal portion 16. An inner element 20, slidingly engaged within elongated channel 14, has a steering mechanism, shown here as actuated by a steering wire 22, configured for selectively deflecting a steerable distal portion 24 of inner element 20.

The provision of a slidable steering mechanism within a multiple-electrode catheter is of great significance. Specifically, as will be described in detail below, the steering mechanism may be sequentially positioned and actuated in order to ensure that one or more electrodes at a time are in effective contact with the adjacent tissue prior to operation of those electrodes, thereby making it possible to reduce or eliminate instances of incomplete ablation. This and other advantages of the present invention will become clearer from the subsequent description.

Parenthetically, it should be noted that, although described primarily in the preferred context of an ablation catheter, the various aspects of the present invention may be used to advantage additionally, or alternatively, for sensing functions, providing sensing at a series of sites spaced along a line which may be useful for mapping and other diagnostic techniques. In most cases, sensing functions may be performed using the same structure, or a similar structure with minor adaptations self-evident to one ordinarily skilled in the art, as is used for ablation procedures. The term "operation" of an electrode is used herein in the description and claims to refer generically to operation as a sensor, operation as an ablating electrode by supply of suitable RF power, and any other mode of operation of an electrode.

Turning now to the structural features of the preferred implementation of FIGS. 1A and 1B in more detail, the steering mechanism is preferably configured to be selectively operable from an initial curved form so as to tend to straighten the steerable distal portion. In other words, the steering mechanism preferably has the capability of providing a straightening force when bent "backwards", i.e., against the direction of curvature normally induced by actuation of the steering mechanism. In a steering mechanism of the type illustrated in FIG. 1B where steering is achieved by pulling on a steering wire 22, this is achieved by localizing the wire along one side of the inner element. In the example illustrated in FIG. 1B, this is done by locating steering wire 22 within a lumen 26 extending along steerable distal portion 24. Along the remainder of the length of inner element 20 outside proximal to distal portion 24, steering wire 22 passes along the catheter within a central region of inner element 20, typically confined within a compression coil, as is well known in the art.

For reasons which will become clear below in the context of FIG. 3, it is a particularly preferred feature that the length L of the operative portion of the steering mechanism corresponds to the spacing between pairs of electrodes. In more precise terms, if flexible distal portion 16 features n electrodes spaced evenly at an interval d (n being at least 3), L is preferably approximately equal to m×d where m is a positive integer less than n, such that the distal end and the proximal end of the steerable distal portion come into simultaneous functional alignment with pairs of the electrodes. Most preferably, m is no more that half of n such that each one of the electrodes is spaced by L from at least one other of the electrodes.

By way of example, in the schematic example shown here, hollow catheter 12 has ten electrodes 16 (i.e., n=10) and the operative portion of the steering mechanism (i.e., distal steerable portion 24) has a length L=5d. As a result, inner element 20 can assume five indexing position in which the proximal and distal ends of distal steerable portion 24 are each functionally aligned with one electrode, thereby defining five pairs of electrodes. In practice, the catheter assembly may often be implemented with significantly more numerous electrodes than are shown here.

It should be noted that, in addition to the highly advantageous combination of a slidable steering mechanism within a multiple-electrode catheter, the present invention provides two further sets of highly significant features each of which may be used independently to advantage, but which are believed to be of particular significance when combined with the slidable steering mechanism described thus far. The first of these relates to the use of slidable electrical contacts, while the second relates to the use of slidable locating elements. These features will now be described in a preferred implementation in combination with the features already described in FIG. 1B.

Thus, inner element 20 preferably further includes at least one, and preferably two, outwardly facing electrical contacts 28. Each electrical contact 28 is configured such that, by moving inner element 20 along channel 14, electrical contact 28 is selectively brought into alignment for forming an electrical connection with one of a number of different electrodes 18. This allows a single electrical connecting wire 30 for each contact to be used to operate a sequence of different electrodes 18, thereby greatly reducing the complexity of electrical wiring required and consequently reducing the unit cost of the catheter assembly.

Structurally, electrical contacts 28 may be implemented in various different forms. Most simply, the contacts may be provided by spring contacts permanently biased outwards towards internal contact surfaces of electrodes 18. Alternatively, a deployment mechanism, such as for example an inflatable balloon actuator (not shown), may be used to selectively displace the contacts outwards when required and allow retraction of the electrodes prior to adjusting the position of the inner element 20. These and other implementations are within the capabilities of one ordinarily skilled in the art.

Where more than one electrical contact 28 is used, the spacing between the contacts is preferably equal to an integer multiple of the electrode spacing d to allow operation of more than one electrode while inner element 20 remains in one position. Preferably, electrical contacts 28 are aligned with one, or most preferably both, ends of steerable distal portion 24, thereby inherently ensuring that the electrodes to be operated are the same electrodes with which the steering mechanism is aligned to ensure tissue contact.

Turning now to the use of slidable locating elements, inner element preferably also includes at least one locating element 32 forming part of a location sensing system for determining a position of at least one point in inner element 20. Other elements of the location sensing system, which does not per se constitute part of the invention, are not illustrated. Locating element 32 is either a transmitting element or a receiving element electrically connected by a sensor connection wire 34 extending along the length of inner element 20.

The location sensing system is preferably a system which provides accurate position information in at least three dimensions, and most preferably in six dimensions. The system preferably generates coordinates in a coordinate frame which is reproducibly related to the body position of the subject. The location sensing system is preferably a non-imaging system, i.e., which operates without requiring simultaneous activation of any imaging device. A most preferred implementation of the invention employs a location sensing system as described in co-assigned PCT Publications Nos. WO00/16684 or WO00/10456 which are incorporated by reference herein.

When used in combination with the slidable steering mechanism, a locating element 32 is preferably located at one, and most preferably both, ends of steerable distal portion 24, thereby inherently ensuring that the locating elements sense the position of the electrodes which the steering mechanism is aligned to ensure tissue contact. Similarly, when used in combination with the slidable contacts, a locating element 32 is preferably located adjacent to each electrical contact 28, thereby inherently ensuring that the locating elements sense the position of the electrodes to be operated.

Clearly, the use of slidable locating elements 32 which are selectively brought adjacent to electrodes prior to operation of those electrodes offers significant advantages. Firstly, precise location information is available for each electrode such that, in the event of an ineffective ablation (as identified by monitoring parameters of the process, such as current, voltage, and temperature), a single tip probe may subsequently be brought accurately to the problematic site. This allows a single-electrode steerable ablation catheter to be brought precisely to the point in the line at which incomplete ablation occurred and to perform a supplementary ablation step in order to complete the desired line of treatment. At the same time, the number of locating elements required, as well as the complexity of the wiring, is greatly reduced, thereby rendering the catheter assembly highly cost effective.

Turning now to the operation of catheter assembly 10 and the corresponding method, FIGS. 2A–2F illustrate a sequence of steps through which the catheter assembly is guided to a position in which each of the electrodes lies adjacent to a corresponding region of tissue, in this case, forming a ring around the left atrium.

Figure 2A:
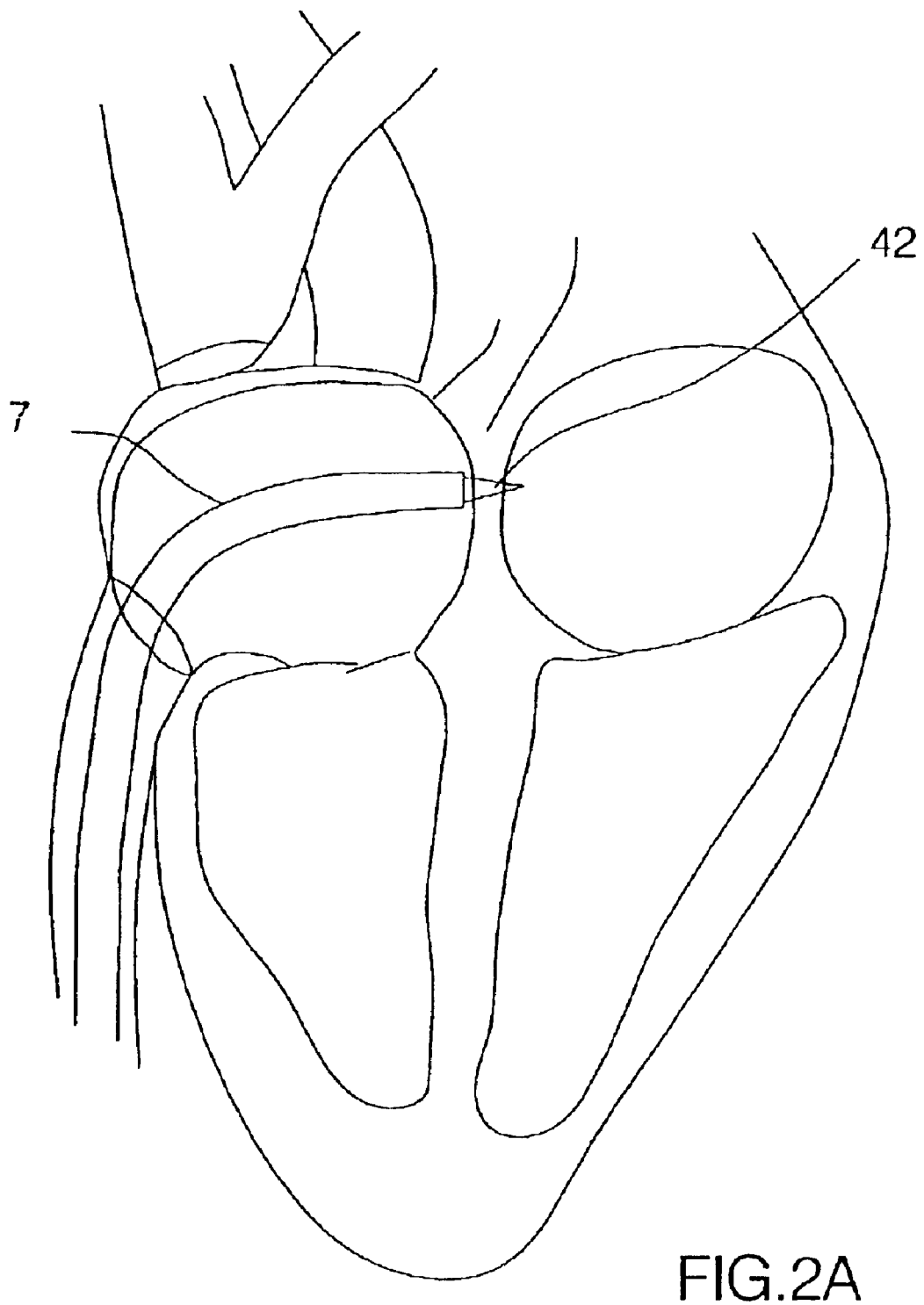
FIGS. 2A–2F are a sequence of schematic cross-sectional views showing steps of a procedure performed using the catheter assembly of FIGS. 1A and 1B.
Figure 2B:
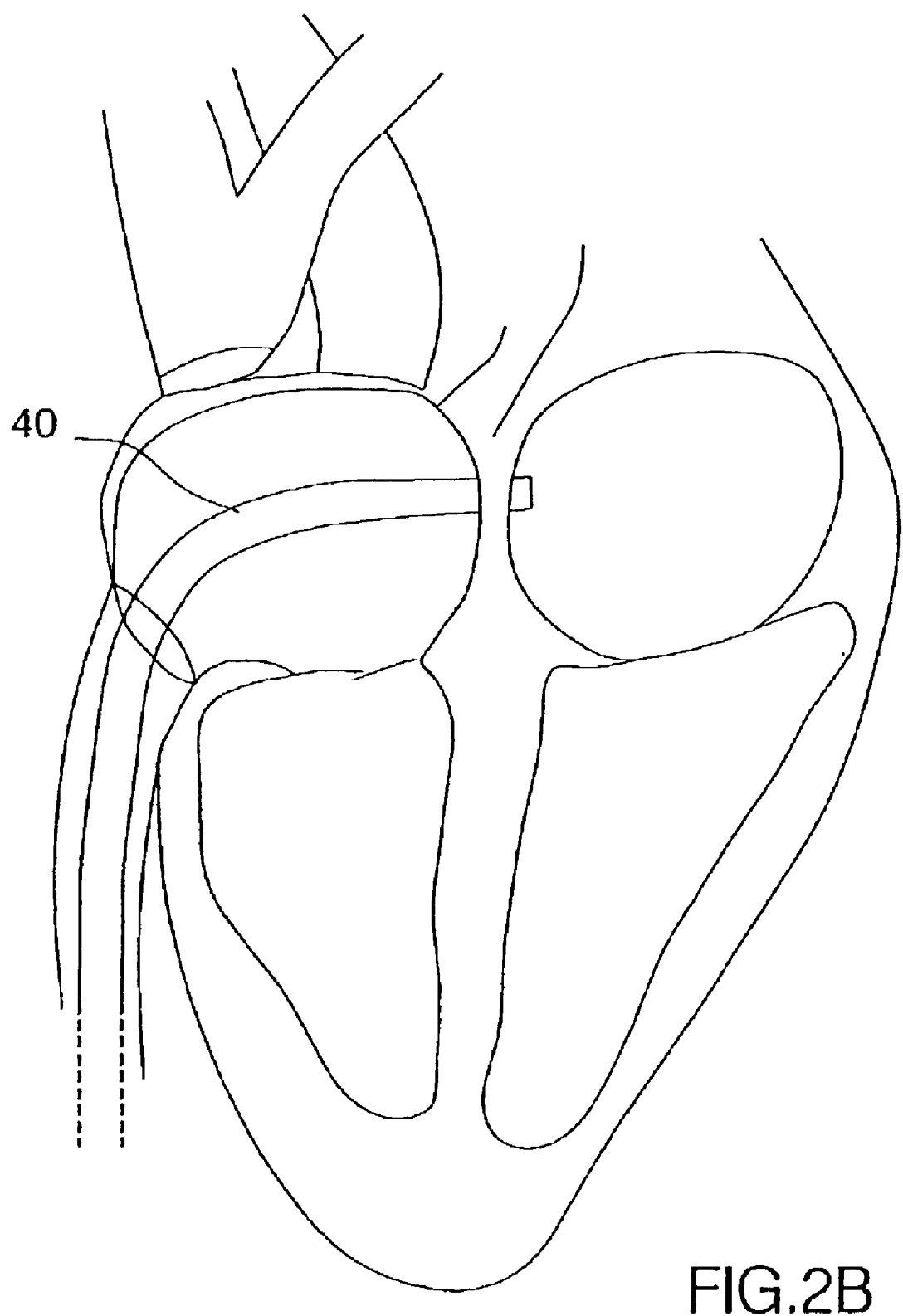
Figure 2C:
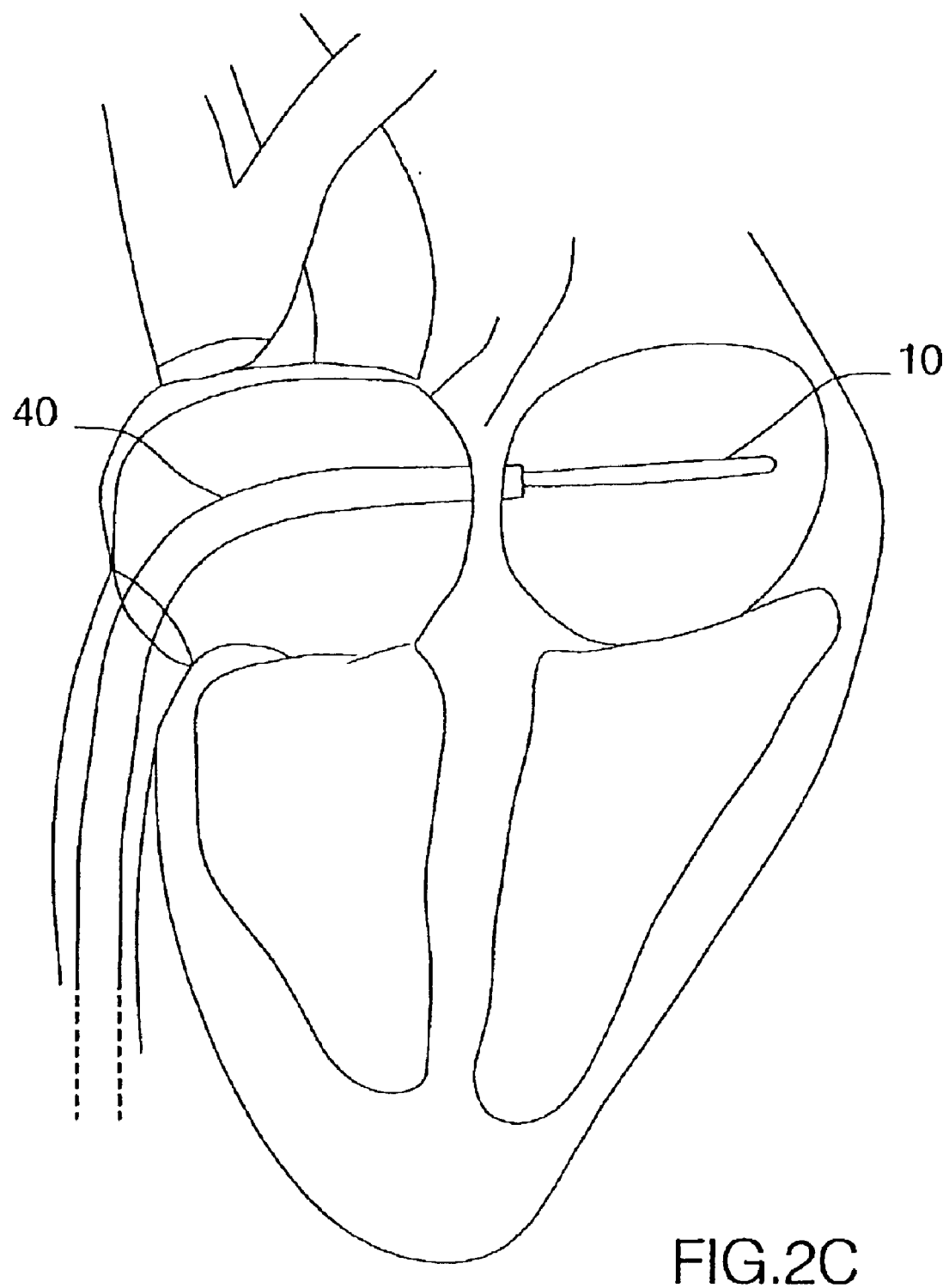
Figure 2D:
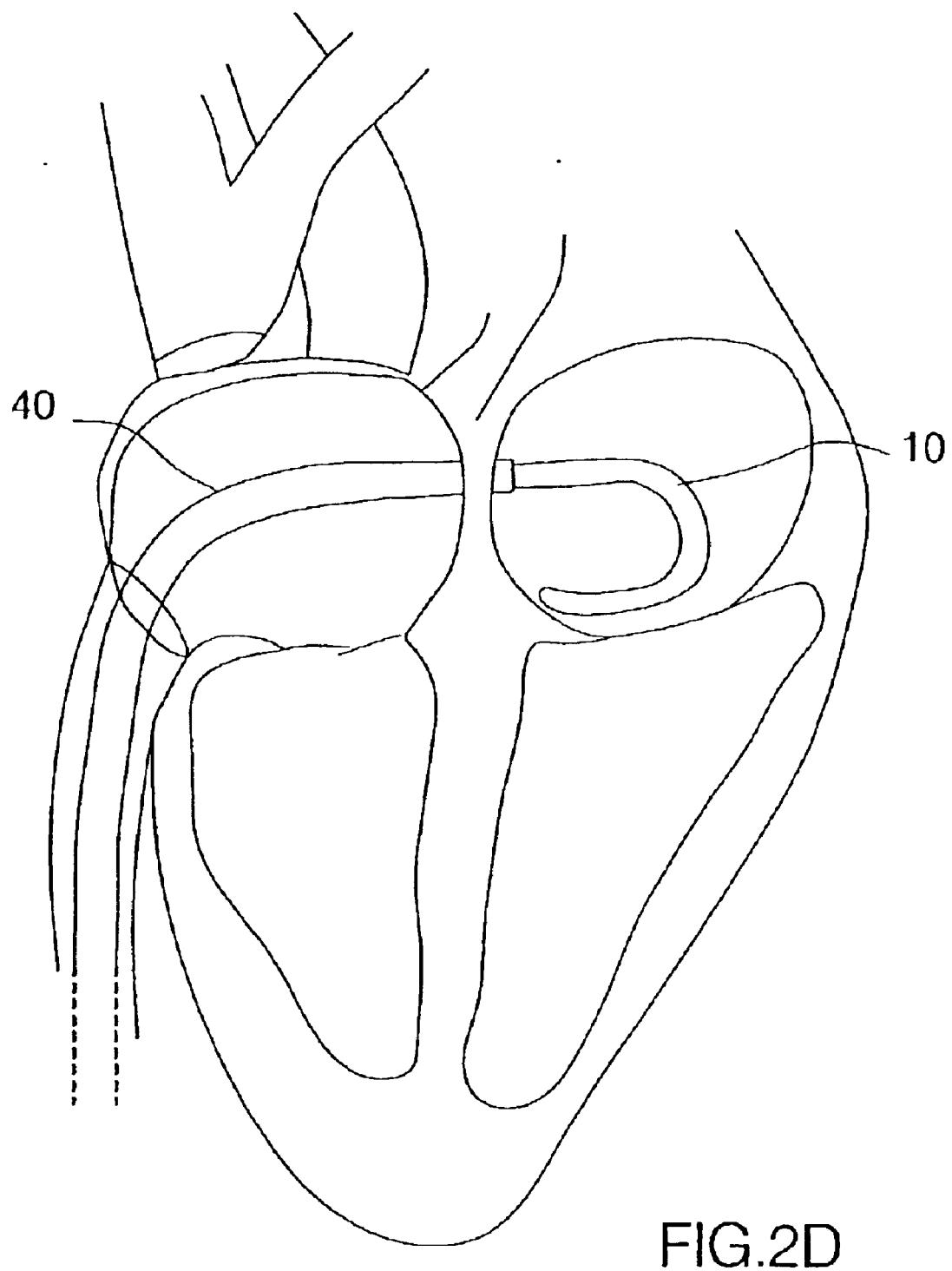
Figure 2E:
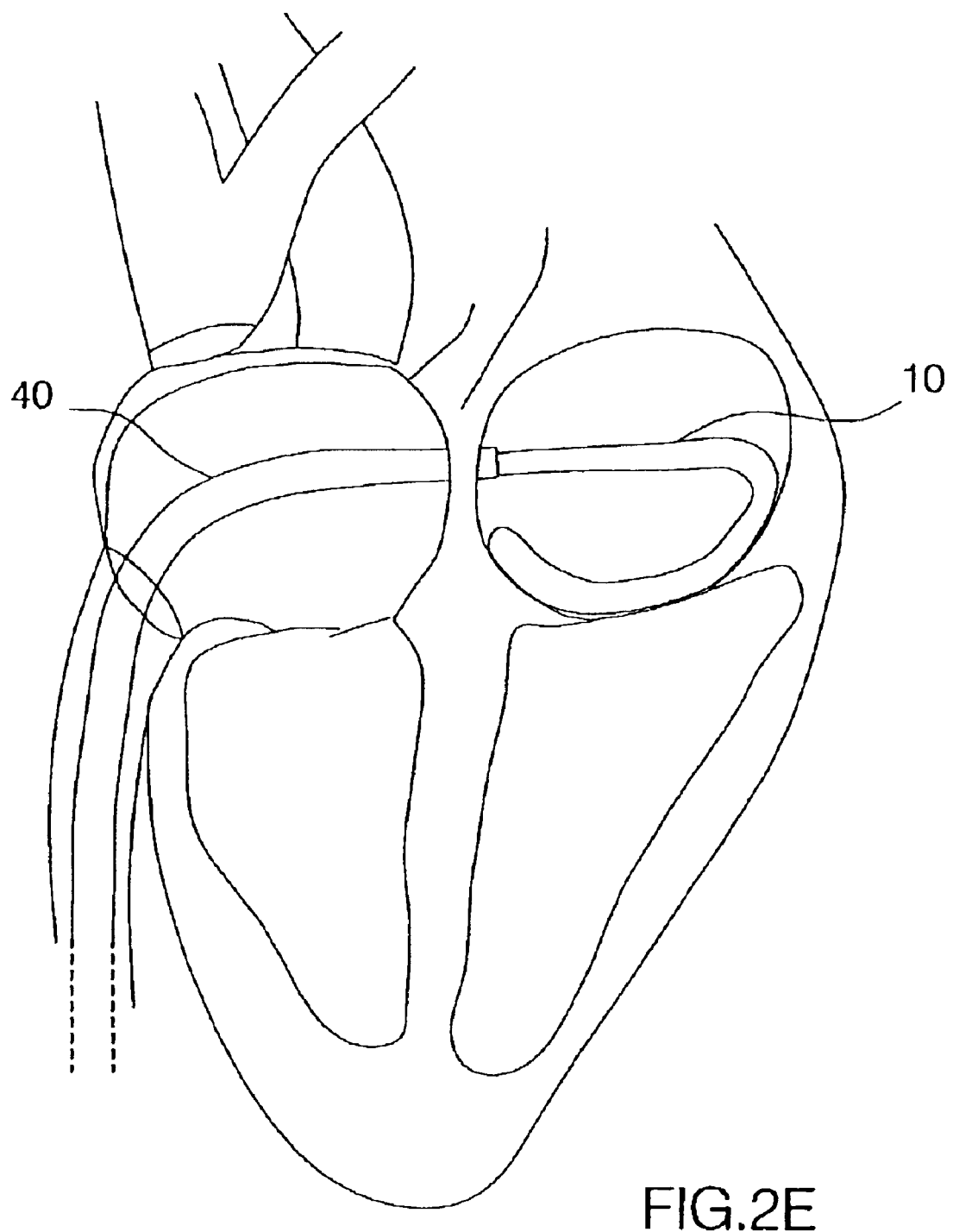
Figure 2F:
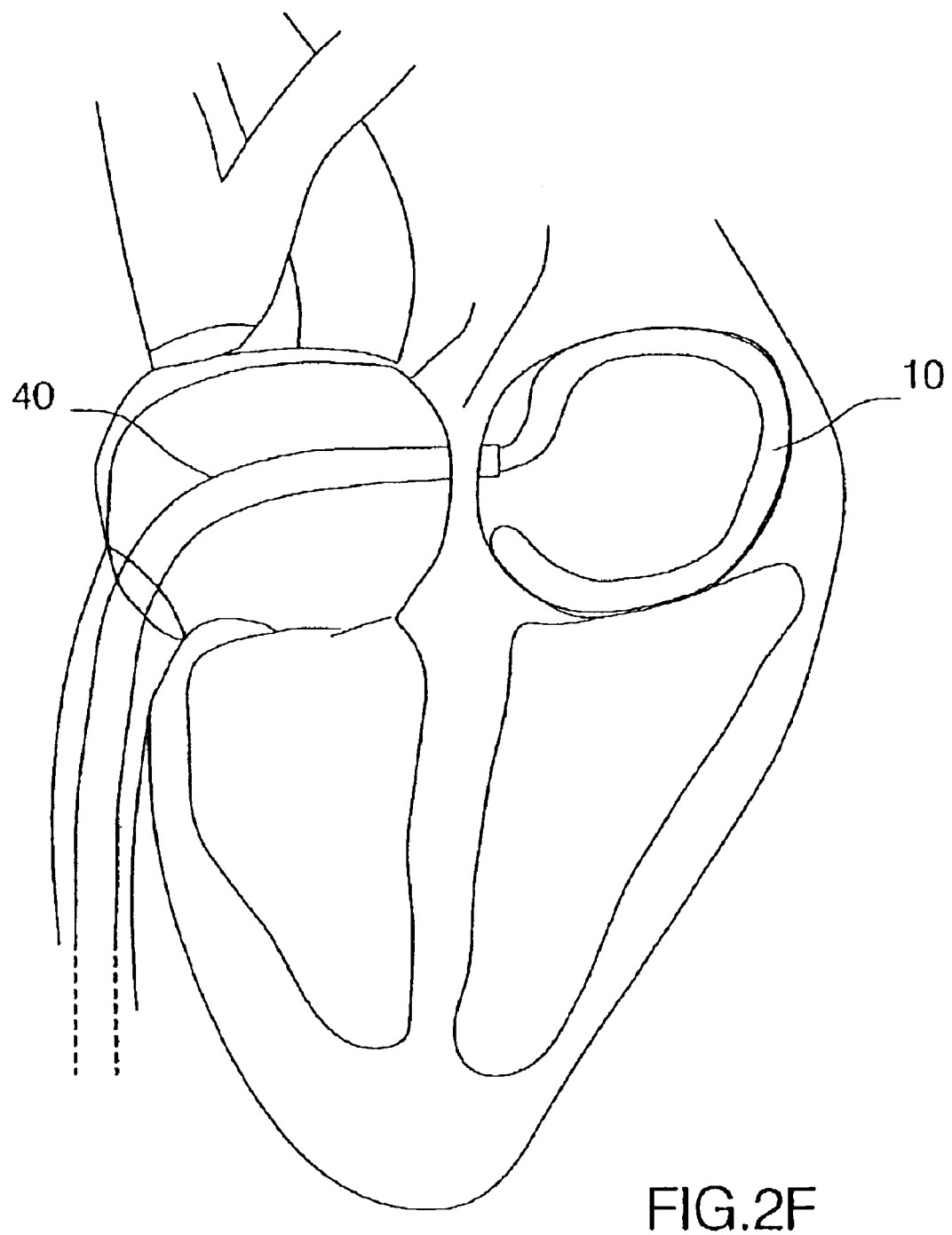

Specifically, an external guide sheath 40 is first navigated to the left atrium. This is typically achieved by entering the right atrium via the IVC and piercing the septum by use of a needle 42 (FIG. 2A). The needle 42 is then withdrawn and sheath 40 is advanced into the left atrium (FIG. 2B). Catheter assembly 10 is then introduced through sheath 40 (FIG. 2C) and is flexed, typically by operation of the steering mechanism of inner element 20, so that the distal extremity of hollow catheter 12 lies near the point of introduction into the atrium. The steering mechanism is then released as the catheter is advanced, thereby gradually deploying distal portion 16 along a line around the internal tissue surface of the atrium (FIGS. 2E and 2F).

Figure 3:
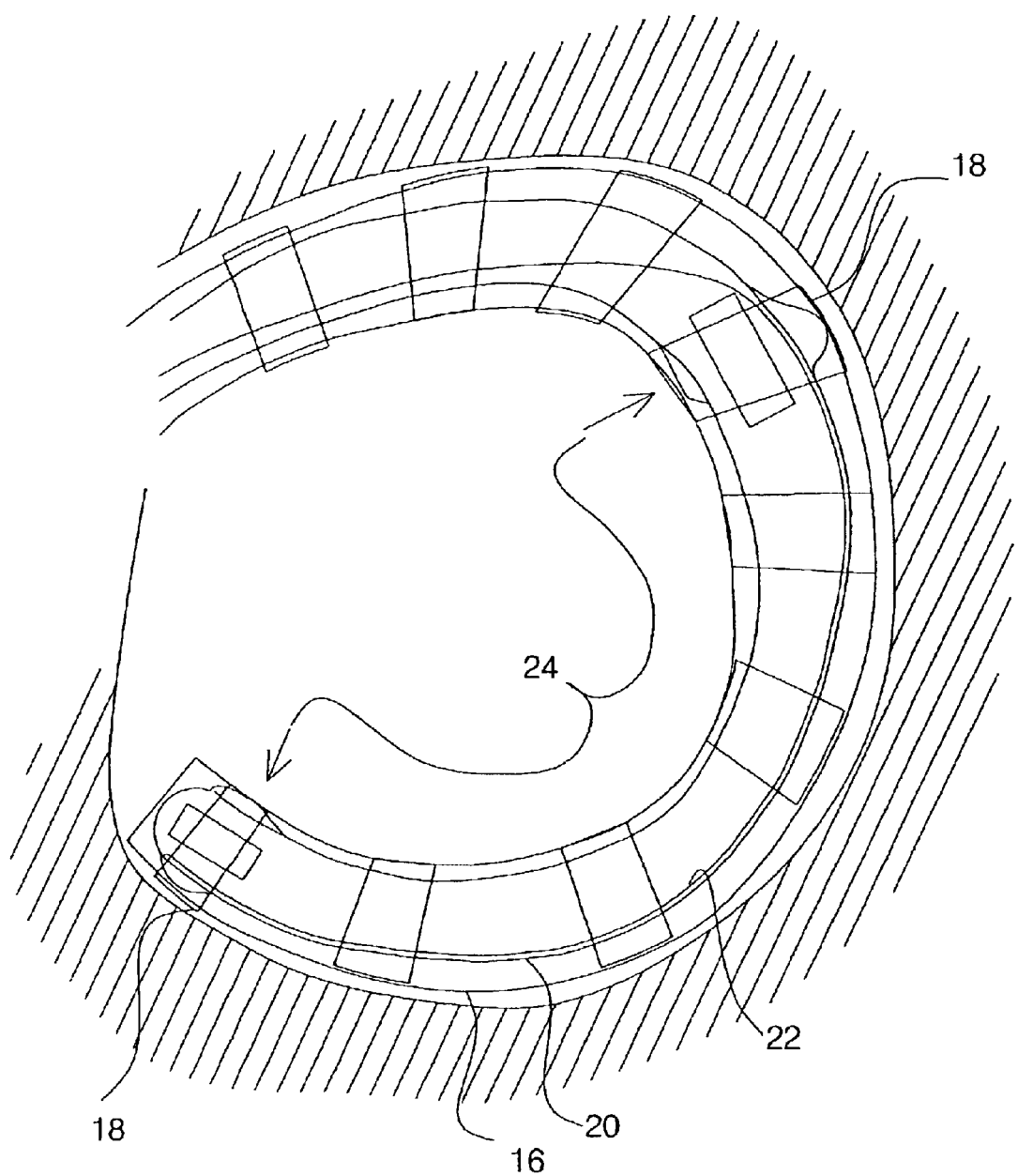
FIG. 3 is a schematic enlargement of part of FIG. 2F illustrating the use of a steering mechanism of the catheter assembly to ensure effective contact of electrodes with adjacent tissue during operation.

At this point, the steering mechanism is rotated, preferably by rotating inner element 20 while holding hollow catheter 12 still so as not to disturb the catheter positioning, so that steering wire 22 extends along the outside of the curve of distal portion as shown in FIG. 3. As a result, tension applied to steering wire 22 tends to straighten steerable distal portion 24, thereby tending to push outwards electrodes 18 adjacent to the ends of steerable distal portion 24. This ensures effective contact between the selected pair of electrodes and the adjacent tissue. For operation of a series of electrodes, the inner element 20 is slid to a sequence of positions and actuated so as to each time ensure effective contact of one, or preferably a pair, of electrodes 18 with the corresponding region of tissue during operation.

Figure 4A:
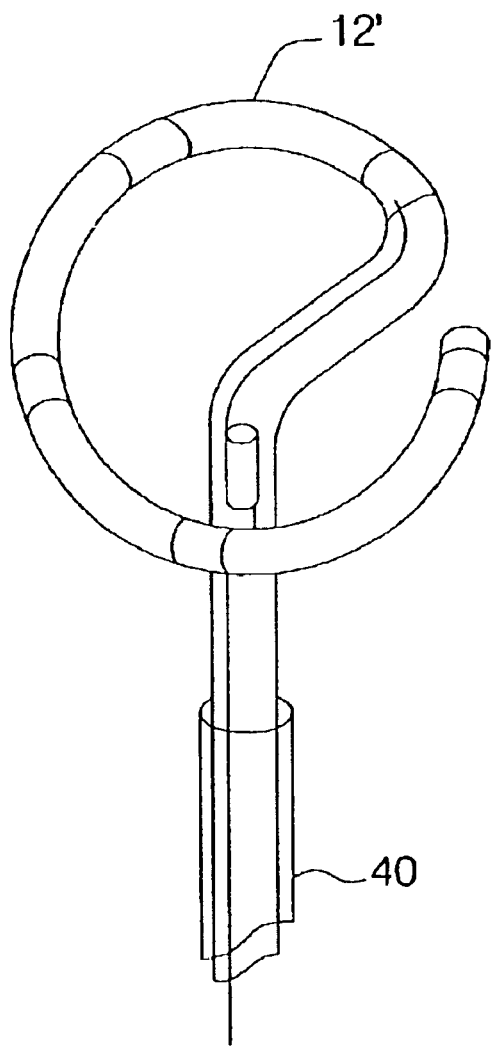
FIGS. 4A and 4B are schematic cross-sectional views taken through a variant implementation of the catheter assembly of FIGS. 1A and 1B in a deployed state and a retracted state, respectively.
Figure 4B:
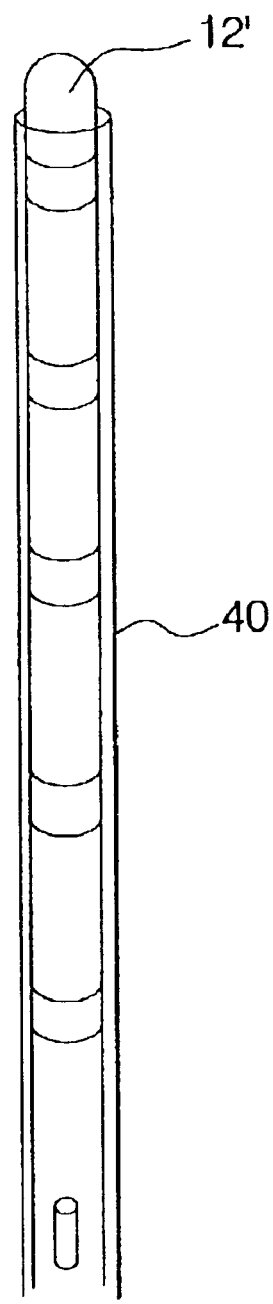

Turning now briefly to FIGS. 4A and 4B, it should be noted that mechanisms other than the steering mechanism of inner element 20 may alternatively be used to deploy hollow catheter 12 adjacent to the intended tissue. By way of example, FIG. 4A shows a variant implementation of the present invention in which hollow catheter 12' is implemented with a shape memory configured to facilitate positioning for performing an ablation procedure requiring a line of a particular predefined shape, for instance a circular ablation around the pulmonary vein ostium. FIG. 4B shows the same catheter withdrawn in a straight configuration within a sheath 40 ready for deployment.

It will be appreciated that the above descriptions are intended only to serve as examples, and that many other embodiments are possible within the spirit and the scope of the present invention.

What is claimed is:

1. A multiple-electrode catheter assembly comprising:
   (a) a hollow catheter having an internal elongated channel and a flexible distal portion, a plurality of electrodes being spaced along said flexible distal portion; and
   (b) an inner element slidingly engaged within said elongated channel, said inner element having a steering mechanism configured for selectively deflecting a steerable distal portion of said inner element and wherein said inner element further includes at least one outwardly facing electrical contact, said electrical contact being configured such that, by moving said inner element along said internal elongated channel, said electrical contact is selectively brought into alignment for forming an electrical connection with each of at least two of said plurality of electrodes.

2. The catheter assembly of claim 1, wherein said steering mechanism is configured to be selectively operable from an initial curved form so as to tend to straighten said steerable distal portion.

3. The catheter assembly of claim 1, wherein said plurality of electrodes is implemented as n electrodes spaced evenly at an interval d along said flexible distal portion, n being at least 3, and wherein a distal end and a proximal end of said steerable distal portion are separated by a length L along said inner element, L being approximately equal to m×d where m is a positive integer less than n, such that said distal end and said proximal end of said steerable distal portion come into simultaneous functional alignment with pairs of said electrodes.

4. The catheter assembly of claim 3, wherein m is no more that half of n such that each one of said electrodes is spaced by L from at least one other of said electrodes.

5. The catheter assembly of claim 3, wherein said inner element further includes a distal electrical contact located at said distal end of said distal steerable portion and a proximal electrical contact located at said proximal end of said distal steerable portion, said distal and said proximal electrical contacts being configured such that, by moving said inner element along said internal elongated channel, said distal and proximal electrical contacts are selectively brought into alignment for forming an electrical connection with said pairs of said plurality of electrodes.

6. The catheter assembly of claim 5, wherein said inner element further includes a distal locating element located at said distal end of said distal steerable portion and a proximal locating element located at said proximal end of said distal steerable portion, said distal and said proximal locating elements forming parts of a location sensing system for determining positions of said distal end and said proximal end, respectively, of said steerable distal portion.

7. The catheter assembly of claim 3, wherein said inner element further includes a distal locating element located at said distal end of said distal steerable portion and a proximal locating element located at said proximal end of said distal steerable portion, said distal and said proximal locating elements forming parts of a location sensing system for determining positions of said distal end and said proximal end, respectively, of said steerable distal portion.

8. The catheter assembly of claim 1, wherein said at least one outwardly facing electrical contact includes a distal electrical contact located at a distal end of said distal steerable portion.

9. The catheter assembly of claim 1, wherein said at least one outwardly facing electrical contact includes a proximal electrical contact located at a proximal end of said distal steerable portion.

10. The catheter assembly of claim 1, wherein said inner element further includes at least one locating element forming part of a location sensing system for determining a position of at least one point in said inner element.

11. The catheter assembly of claim 10, wherein said at least one locating element includes a distal locating element located at a distal end of said distal steerable portion.

12. The catheter assembly of claim 10, wherein said at least one locating element includes a proximal locating element located at a proximal end of said distal steerable portion.

13. The catheter assembly of claim 10, wherein said at least one locating element forms part of a locating system which determines said position of at least one point in said inner element in three dimensions.

14. The catheter assembly of claim 10, wherein said at least one locating element forms part of a locating system which is a non-imaging locating system.

15. The catheter assembly of claim 10, wherein said at least one locating element forms part of a locating system which generates coordinates of said position of at least one point relative to a given frame of reference.

16. A multiple-electrode catheter assembly comprising:

(a) a hollow catheter having an internal elongated channel and a hollow distal portion, a plurality of electrodes being spaced along said hollow distal portion; and (b) an inner element slidingly engaged within said elongated channel, said inner element having an actuating distal portion including at least one outwardly facing electrical contact, said electrical contact being configured such that, by moving said inner element along said internal elongated channel, said electrical contact is selectively brought into alignment for forming an electrical connection with each of at least two of said plurality of electrodes.

17. The catheter assembly of claim 16, wherein said plurality of electrodes is implemented as n electrodes spaced evenly at an interval d along said flexible distal portion, n being at least 3, and wherein said at least one electrical contact includes a distal electrical contact and a proximal electrical contact separated by a length L along said inner element, L being equal to m×d where m is a positive integer less than n, such that said distal electrical contact and said proximal electrical contact of said actuating distal portion come into simultaneous alignment with pairs of said electrodes.

18. The catheter assembly of claim 16, wherein said inner element further includes a locating element associated with said at least one electrical contact, said locating element forming part of a location sensing system for determining a position of said at least one electrical contact.

19. The catheter assembly of claim 18, wherein said at least one locating element forms part of a locating system which determines said position of at least one point in said inner element in three dimensions.

20. The catheter assembly of claim 18, wherein said at least one locating element forms part of a locating system which is a non-imaging locating system.

21. The catheter assembly of claim 18, wherein said at least one locating element forms part of a locating system which generates coordinates of said position of at least one point relative to a given frame of reference.

22. A multiple-electrode catheter assembly comprising:

(a) a hollow catheter having an internal elongated channel and a hollow distal portion, a plurality of electrodes being spaced along said hollow distal portion; and (b) an inner element slidingly engaged within said elongated channel, said inner element having a sensing distal portion including at least one locating element, said locating element forming part of a location sensing system for determining a position of at least one point within said inner element, such that, by moving said inner element along said internal elongated channel, said locating element is selectively brought into alignment for determining the position of each of at least two of said plurality of electrodes.

23. The catheter assembly of claim 22, wherein said plurality of electrodes is implemented as n electrodes spaced evenly at an interval d along said flexible distal portion, n being at least 3, and wherein said at least one locating element includes a distal locating element and a proximal locating element separated by a length L along said inner element, L being equal to m×d where m is a positive integer less than n, such that said distal locating element and said proximal locating element of said sensing distal portion come into simultaneous alignment with pairs of said electrodes.

24. The catheter assembly of claim 22, wherein said at least one locating element forms part of a locating system which determines said position of at least one point in said inner element in three dimensions.

25. The catheter assembly of claim 22, wherein said at least one locating element forms part of a locating system which is a non-imaging locating system.

26. The catheter assembly of claim 22, wherein said at least one locating element forms part of a locating system which generates coordinates of said position of at least one point relative to a given frame of reference.

27. A method for performing a procedure using a multiple-electrode assembly, the method comprising:

(a) providing a hollow catheter having a distal portion with a plurality of independently operable electrodes;

(b) deploying a steering mechanism within said hollow catheter so as to be slidable along a length of said distal portion;

(c) guiding the catheter to a position in which each of the electrodes lies adjacent to a corresponding region of tissue;

(d) sliding the steering mechanism along said distal portion to a first position and actuating the steering mechanism so as to ensure effective contact of at least a first of said electrodes with the corresponding region of tissue during operation of said first electrode; and (e) sliding the steering mechanism along said distal portion to a second position and actuating the steering mechanism so as to ensure effective contact of at least a second of said electrodes with the corresponding region of tissue during operation of said second electrode.

28. The method of claims 27, wherein the catheter assumes a curved configuration when in said position in which each of the electrodes lies adjacent to a corresponding region of tissue, and wherein the steering mechanism is actuated so as to tend to straighten a selected part of said distal portion.

29. The method of claims 27, wherein the plurality of electrodes are implemented as n electrodes spaced evenly at an interval d along the distal portion, n being at least 3, and wherein the steering mechanism has an operative portion of length L, L being approximately equal to m×d where m is a positive integer less than n, such that a distal end and a proximal end of the operative portion of the steering mechanism come into simultaneous functional alignment with pairs of said electrodes.

30. The method of claim 27, further comprising providing a locating system including at least one element associated with the steering mechanism, the locating system determining a current location of at least one electrode which the steering mechanism is currently maintaining in contact with the corresponding region of tissue.

31. The method of claim 27, further comprising providing at least one electrical contact associated with the steering mechanism and moving the electrical contact together with the steering mechanism along the distal portion such that the electrical contact is successively brought into alignment for forming an electrical connection with each of at least two of the plurality of electrodes.

* * * * *